(12) United States Patent
Hachiya et al.

(10) Patent No.: US 6,858,764 B2
(45) Date of Patent: Feb. 22, 2005

(54) METHOD FOR PREPARING BROMOFLUORENES

(75) Inventors: Tetsuo Hachiya, Tokyo (JP); Naoyuki Kitamura, Tokyo (JP); Hiroaki Mori, Tokyo (JP); Toshiyuki Yasuda, Tokyo (JP)

(73) Assignee: JFE Chemical Corporation, Tokyo (JP)

( * ) Notice: Subject to any disclaimer, the term of this patent is extended or adjusted under 35 U.S.C. 154(b) by 138 days.

(21) Appl. No.: 10/244,681

(22) Filed: Sep. 17, 2002

(65) Prior Publication Data

US 2003/0065226 A1 Apr. 3, 2003

(30) Foreign Application Priority Data

Sep. 28, 2001 (JP) .................................... 2001-301890

(51) Int. Cl.[7] .............................................. C07C 22/00
(52) U.S. Cl. ...................................................... 570/184
(58) Field of Search .......................................... 570/184

(56) References Cited

U.S. PATENT DOCUMENTS 6,344,585 B2   2/2002   Mori

OTHER PUBLICATIONS

Adolf Sieglitz, "Studien in Der Fluoren–Reihe," Berichte d. D. Chem. Gesellschaft, May 6, 1920, pp. 1232–1241.

G. Hallas, et al. "Extended Conjugation in Di– and Tri–Arylmethanes. Part I. Electronic Absorption Spectra of 9,9–Dimethylfluorene Analouges of Crystal Violet and Malachite Green" J. Chem. Soc. 1970, pp. 975–979.

Charles J. Kelley, et al. "Synthesis of Bridged Oligophenylenes from Fluorene. Part 1. Ter –and Quarter–Phenyls," J. Chem.Research (S) and J. Chem. Research (M), 1997, pp. 446–447 and pp. 2701–2733.

Maxime Ranger, et al. "New Well–Defined Poly(2,7–Fluorene) Derivatives: Photoluminescene and Base Doping" Macromolecules, 30, 1997, pp. 7686–7691.

F. K. Sutcliffe, et al. "The Synthese and Properties of Dyes and Pigments Containing A 9,9–Spirobifluorene Residue" JSDC, Jul. 1978, pp. 306–309.

Ruilian Wu, et al. "Convergent Synthetic Routes to Orthogonally Fused Conjugated Oligomers Directed Toward Molecular Scale Electronic Device Applications" J. Org. Chem, 1996, pp. 6906–6921.

*Primary Examiner*—Paul J. Killos
(74) *Attorney, Agent, or Firm*—Oblon, Spivak, McClelland, Maier & Neustadt, P.C.

(57) ABSTRACT

A method for preparing bromofluorenes includes a step of dispersing a compound selected from the group consisting of fluorene, fluorenone, and derivatives of fluorene and fluorenone in water to prepare a disperse system. Bromination is initiated by adding bromine $Br_2$ into the disperse system. Thus, bromofluorenes can be efficiently and economically prepared without using any environmentally harmful organic solvent requiring a high cost to dispose of.

5 Claims, No Drawings

METHOD FOR PREPARING BROMOFLUORENES

BACKGROUND OF THE INVENTION

1. Field of the Invention

The present invention relates to methods for preparing bromofluorenes, which are useful as intermediate products or functional resins.

2. Description of the Related Art

For preparing bromofluorenes, methods are known which use halogenated hydrocarbons as solvents to brominate fluorene compounds. These methods are published in, for example, the following literatures: A. Sieglitz, Ber. Dtsch. Chem. Ges., 53, 1232 (1920); G. Hallas, J. D. Hepworth, D. R. Woring, J. Chem. Soc. (B), 975 (1970); C. J. Kelley, A. Ghiorghis, J. M. Kaurffman, J. Chem. Reserch(S), 446 (1997); M. Ranger, D. Rondeau, M. Leclerc, Macromolecules, 30, 7686 (1997); F. K. Sutcliffe, H. M. Shahidi, D. Patterson, J. Soc. Dyers Colour, 94 (7), 306 (1978); and R. Wu, J. S. Schumm, D. L. Pearson, J. M. Tour, J. Org. Chem., 61 (20), 6906 (1996).

Methods are also known which use organic solvents other than halogenated hydrocarbons, such as dimethylformamide. These methods are published in, for example, the following literatures: M. Ranger, D. Rondeau, M. Leclerc, Macromolecules, 30, 7686 (1997); and D. M. Johansson, M. Theander, T. Granlund, O. Inganas, M. R. Andersson, ibid., 34, 1981 (2001).

However, halogenated hydrocarbons have deleterious effects on the environment and the handling of such organic solvents is burdensome. Other solvents also have a problem in that it is enormously costly to dispose of them and waste water containing the solvents.

SUMMARY OF THE INVENTION

Accordingly, an object of the present invention is to provide an efficient and economical method for preparing bromofluorenes in which no environmentally harmful organic solvent requiring a high cost to dispose of is used.

To this end, according to an aspect of the present invention, a method for preparing bromofluorenes is provided. The method includes a step of dispersing a compound selected from the group consisting of fluorene, fluorenone, and derivatives of fluorene and fluorenone in water to prepare a disperse system. Fluorene, fluorenone, and their derivatives are here collectively referred to as fluorene compounds. The method also includes a step of adding bromine $Br_2$ into the disperse system to conduct bromination.

DESCRIPTION OF THE PREFERRED EMBODIMENTS

The present invention will be further illustrated in detail with reference to preferred embodiments.

Fluorene compounds used as a raw material in the present invention include fluorene, fluorenone, 9-alkylfluorenes and 9,9-dialkylfluorenes expressed by formula 1, and spirobifluorenes expressed by formula 2. Alkyl groups in formulas 1 and 2 have carbon numbers in the range of 1 to 22, and include the methyl group, the ethyl group, the propyl group, the butyl group, the pentyl group, the hexyl group, the heptyl group, the octyl group, the nonyl group, the decyl group, the dodecyl group, the tetradecyl group, the hexadecyl group, the octadecyl group, the eicosyl group, the docosyl group, the isobutyl group, and the 2-ethylhexyl group.

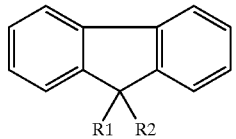

Formula 1

R1 and R2 in formula 1 each represent a hydrogen atom or an alkyl group having a carbon number in the range of 1 to 22.

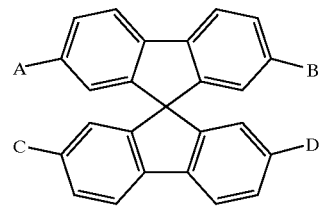

Formula 2

A, B, C, and D in formula 2 each represent a hydrogen atom or a halogen atom.

The above-described alkylfluorenes are produced by alkylating fluorene or a 9-alkylfluorene with an alkyl halide in the presence of a base. Exemplary 9-alkylfluorenes include 9-methylfluorene, 9-ethylfluorene, 9-propylfluorene, 9-butylfluorene, 9-pentylfluorene, 9-hexylfluorene, 9-heptylfluorene, 9-octylfluorene, 9-nonylfluorene, 9-decylfluorene, 9-dodecylfluorene, 9-tetradecylfluorene, 9-hexadecylfluorene, 9-octadecylfluorene, 9-eicosylfluorene, 9-docosylfluorene, 9-isobutylfluorene, and 9-(2-ethylhexyl)fluorene.

Exemplary 9,9-dialkylfluorenes include 9,9-dimethylfluorene, 9,9-diethylfluorene, 9,9-dipropylfluorene, 9,9-dibutylfluorene, 9,9-dipentylfluorene, 9,9-dihexylfluorene, 9,9-diheptylfluorene, 9,9-dioctylfluorene, 9,9-dinonylfluorene, 9,9-didecylfluorene, 9,9-didodecylfluorene, 9,9-ditetradecylfluorene, 9,9-dihexadecylfluorene, 9,9-dioctadecylfluorene, 9,9-didicosylfluorene, 9,9-didocosylfluorene, 9,9-diisobutylfluorene, and 9,9-bis(2-ethylhexyl)fluorene, 9-methyl-9-hexylfluorene, 9-methyl-9-octylfluorene, 9-methyl-9-dodecylfluorene, and 9-methyl-9-eicosylfluorene.

The spirobifluorenes expressed by formula 2 result from a fluorene compound and a 2-halogenated biphenyl, as published by F. K. Sutcliffe, H. M. Shahidi, and D. Patterson in J. Soc. Dyers Colour, 94 (7), 306 (1978). Exemplary spirobifluorenes include 9,9'-spirobifluorene, 2-bromo-9,9'-spirobifluorene, and 2,7-dibromo-9,9'-spirobifluorene.

In the method of the present invention, bromine is used as a brominating agent. The bromine is added to a fluorene compound dispersed in water to brominate the fluorene compound.

In the method of the present invention, by adequately setting the ratio of the raw material fluorene compound to the bromine and varying the reaction conditions such as temperature and time, monobromofluorenes, dibromofluorenes, tribromofluorenes, and the like can be obtained as main products, according to need. In general, the fluorene ring is brominated at the 2- and 7-positions, consequently resulting in mainly 2-bromofluorenes, which are monobromofluorenes, and 2,7-dibromofluorenes, which are dibromofluorenes. Hence, the method of the present invention is particularly advantageous in preparing 2-bromofluorenes and 2,7-dibromofluorenes.

In order to carry out the bromination in the method of the present invention, the raw material fluorene compound is dispersed in water and allowed to react with bromine. If the raw material fluorene compound is in the solid state such as fluorene, fluorenone, 9,9-dimethylfluorene, and 9,9'-spirobifluorene, the fluorene compound is, preferably, powdered or pulverized and formed into a slurry in order to be dispersed in the water. If the raw material fluorene compound is in the liquid state such as 9,9-dihexylfluorene, 9,9-dioctylfluorene, 9,9-didecylfluorene, and 9,9-bis (2ethylhexy) fluorene, the raw material fluorene compound is, preferably, dispersed by mixing and stirring in the water. At this moment, preferably, a small amount of a surfactant or a phase-transfer catalyst is added to increase the dispersibility or the water affinity of the raw material fluorene compound.

The amount of water in which the raw material fluorene compound is dispersed is not particularly limited. However, an extremely small amount of water cannot serve as a satisfactory dispersion medium. Also, an extremely large amount of water reduces the reaction efficiency. The amount of water is generally in the range of 10 to 2000 parts by weight relative to 100 parts by weight of the raw material fluorene compound.

The amount of bromine is not particularly limited and the required amount of the bromine may be added at one time. Preferably, the bromine is divided into aliquots or dripped so as to be added step by step according to the reaction progress.

Although the reaction temperature of the bromination depends on the material and the other reaction conditions, it must be equal to or higher than the temperature at which the dispersion medium, or water, does not freeze and equal to or lower than the temperature at which the water and the bromine do not vaporize in large quantities. Specifically, the reaction temperature is generally in the range of −20 to 100° C., and preferably in the range of 0 to 60° C. If the bromination generates heat, preferably, the reaction is allowed to proceed while the heat is dissipated. The time required for the bromination depends on the raw material and the other reaction conditions, but is generally in the range of 1 to 48 hours.

Preferably, a catalyst and other additives may be added to accelerate the bromination. Exemplary additives include inorganic acids, such as sulfuric acid, hydrochloric acid, and hydrobromic acid; Lewis acids, such as iron chlorides and zinc chloride; halogens other than bromine, such as iodine ($I_2$); heavy metals, such as iron and nickel; and oxidizers, such as hydrogen peroxide and periodic acid.

The bromination produces a by-product, hydrobromic acid. Preferably, this hydrobromic acid is oxidized to bromine with an oxidizer such as hydrogen peroxide in the reaction system during the bromination, so that the amount of bromine used can be reduced.

After the bromination, the target product is present in a solid phase or an organic phase separate from the aqueous phase in the reaction system. The target product is, therefore, easily recovered from the reaction system with a filter or a separating funnel. The crude reaction product can be purified by a common method, such as extraction, distillation, and recrystallization.

EXAMPLES

The method of the present invention will now be described in detail with reference to examples.

Example 1

2-bromofluorene

In a three-liter flask having four openings equipped with a stirrer, a thermometer, a dropping funnel, and a reflux condenser, respectively, 237 g (1.4 mol) of fluorene, 1 L of water, three drops of a surfactant, and five drops of sulfuric acid were placed and stirred to mix. By adding 230 g (1.4 mol) of bromine into the mixture, a reaction was started. After the reaction had been conducted at room temperature for 5 hours, unreacted bromine was decomposed with an aqueous solution of sodium hydrogen sulfite. The reaction product, which was a light yellow solid, was filtered and thus 334 g of a crude product was obtained. The crude product was dissolved in toluene and was subsequently washed with water and a sodium hydrogencarbonate aqueous solution. The resulting organic liquid was dried using anhydrous magnesium sulfate. After filtration, the liquid was concentrated and then allowed to stand at 0° C., so that a white solid was precipitated. The precipitate was filtered and subsequently washed with toluene, followed by drying. Thus, 287 g (1.1 mol, yield of 82%) of a white solid product was obtained. This product was subjected to gas chromatography and the purity of the product was 98.8%.

Example 2

2,7-dibromofluorene

In a three-liter flask having four openings equipped with a stirrer, a thermometer, a dropping funnel, and a reflux condenser, respectively, 237 g (1.4 mol) of fluorene, 1 L of water, three drops of a surfactant, and five drops of sulfuric acid were placed and stirred to mix. By adding 500 g (3.1 mol) of bromine into the mixture, a reaction was started. After the reaction had been conducted at room temperature for 10 hours, unreacted bromine was decomposed with an aqueous solution of sodium hydrogen sulfite. The reaction product, which was a light yellow solid, was filtered and thus 457 g of a crude product was obtained. The crude product was dissolved in toluene and was subsequently washed with water and a sodium hydrogencarbonate aqueous solution. The resulting organic liquid was dried using anhydrous magnesium sulfate. After filtration, the liquid was concentrated and then allowed to stand at 0° C., so that a white solid was precipitated. The precipitate was filtered and subsequently washed with toluene, followed by drying. Thus, 426 g (1.3 mol, yield of 92%) of a white solid product was obtained. This product was subjected to gas chromatography and the purity of the product was 99.5%.

Example 3

2-bromofluorenone

In a three-liter flask having four openings equipped with a stirrer, a thermometer, a dropping funnel, and a reflux condenser, respectively, 256 g (1.4 mol) of fluorenone, 1 L of water, three drops of a surfactant, and five drops of sulfuric acid were placed and stirred to mix. By adding 250 g (1.6 mol) of bromine into the mixture, a reaction was started. After the reaction had been conducted at 50° C. for 12 hours, unreacted bromine was decomposed with an aqueous solution of sodium hydrogen sulfite. The reaction product, which was a dark yellow solid, was filtered and thus 365 g of a crude product was obtained. The crude product was dissolved in toluene and was subsequently washed with water and a sodium hydrogencarbonate aqueous solution.

The resulting organic liquid was dried using anhydrous magnesium sulfate. After filtration, the liquid was concentrated and then allowed to stand at 0° C., so that a yellow solid was precipitated. The precipitate was filtered and subsequently washed with toluene, followed by drying. Thus, 339 g (1.3 mol, yield of 92%) of a yellow solid product was obtained. This product was subjected to gas chromatography and the purity of the product was 99.4%.

Example 4

2,7-dibromo-9,9-dimethylfluorene

In a three-liter flask having four openings equipped with a stirrer, a thermometer, a dropping funnel, and a reflux condenser, respectively, 253 g (1.3 mol) of 9,9-dimethylfluorene, 1 L of water, three drops of a surfactant, and five drops of sulfuric acid were placed and stirred to mix. By adding 500 g (3.1 mol) of bromine into the mixture, a reaction was started. After the reaction had been conducted at 50° C. for 10 hours, unreacted bromine was decomposed with an aqueous solution of sodium hydrogen sulfite. The target product was extracted from the reaction mixture using toluene, and then washed with water and a sodium hydrogencarbonate aqueous solution. The resulting organic liquid was dried using anhydrous magnesium sulfate. After filtration, the liquid was concentrated and then allowed to stand at 0° C., so that a white solid was precipitated. The precipitate was filtered and subsequently washed with toluene, followed by drying. Thus, 417 g (1.2 mol, yield of 90%) of a white solid product was obtained. This product was subjected to gas chromatography and the purity of the product was 99.2%.

Example 5

2,7-dibromo-9,9-diethylfluorene

In a three-liter flask having four openings equipped with a stirrer, a thermometer, a dropping funnel, and a reflux condenser, respectively, 294 g (1.3 mol) of 9,9-diethylfluorene, 1 L of water, three drops of a surfactant, and three drops of sulfuric acid were placed and stirred to mix. By adding 500 g (3.1 mol) of bromine into the mixture, a reaction was started. After the reaction had been conducted at 50° C. for 10 hours, unreacted bromine was decomposed with an aqueous solution of sodium hydrogen sulfite. The target product was extracted from the reaction mixture using toluene, and then washed with water and a sodium hydrogencarbonate aqueous solution. The resulting organic liquid was dried using anhydrous magnesium sulfate. After filtration, the liquid was concentrated and then allowed to stand at 0° C., so that a white solid was precipitated. The precipitate was filtered and subsequently washed with hexane, followed by drying. Thus, 457 g (1.2 mol, yield of 90%) of a white solid product was obtained. This product was subjected to gas chromatography and the purity of the product was 99.0%.

Example 6

2,7-dibromo-9,9-dihexylfluorene

In a three-liter flask having four openings equipped with a stirrer, a thermometer, a dropping funnel, and a reflux condenser, respectively, 448 g (1.3 mol) of 9,9-dihexylfluorene, 1 L of water, and five drops of sulfuric acid were placed and stirred to mix. By adding 500 g (3.1 mol) of bromine into the mixture, a reaction was started. After the reaction had been conducted at 60° C. for 10 hours, unreacted bromine was decomposed with an aqueous solution of sodium hydrogen sulfite. The target product was extracted from the reaction mixture using hexane, and then washed with water and a sodium hydrogencarbonate aqueous solution. The resulting organic liquid was dried using anhydrous magnesium sulfate. After filtration, the liquid was concentrated and then allowed to stand at 0° C., so that a white solid was precipitated. The precipitate was filtered and subsequently washed with hexane, followed by drying. Thus, 594 g (1.2 mol, yield of 90%) of a white solid product was obtained. This product was subjected to gas chromatography and the purity of the product was 99.3%.

Example 7

2,7-dibromo-9,9-dioctylfluorene

In a five-liter flask having four openings equipped with a stirrer, a thermometer, a dropping funnel, and a reflux condenser, respectively, 617 g (1.6 mol) of 9,9-dioctylfluorene, 2 L of water, and five drops of sulfuric acid were placed and stirred to mix. By adding 600 g (3.8 mol) of bromine into the mixture, a reaction was started. After the reaction had been conducted at 60° C. for 12 hours, unreacted bromine was decomposed with an aqueous solution of sodium hydrogen sulfite. The target product was extracted from the reaction mixture using hexane, and then washed with water and a sodium hydrogencarbonate aqueous solution. The resulting organic liquid was dried using anhydrous magnesium sulfate. After filtration, the liquid was concentrated and then allowed to stand at 0° C., so that a white solid was precipitated. The precipitate was filtered and subsequently washed with hexane, followed by drying. Thus, 797 g (1.5 mol, yield of 93%) of a white solid product was obtained. This product was subjected to gas chromatography and the purity of the product was 99.1%.

Example 8

2,7-dibromo-9,9-bis(2-ethylhexyl)Fluorene

In a one-liter flask having four openings equipped with a stirrer, a thermometer, a dropping funnel, and a reflux condenser, respectively, 111 g (0.28 mol) of 9,9-bis(2-etylhexyl)fluorene, 300 mL of water, and three drops of sulfuric acid were placed and stirred to mix. By adding 100 g (0.63 mol) of bromine into the mixture, a reaction was started. After the reaction had been conducted at 60° C. for 12 hours, unreacted bromine was decomposed with an aqueous solution of sodium hydrogen sulfite. The target product was extracted from the reaction mixture using hexane, and then washed with water and a sodium hydrogencarbonate aqueous solution. The resulting organic liquid was dried using was dried using anhydrous magnesium sulfate. After filtration, the liquid was concentrated by distilling the solvent, thus resulting in 151 g of a crude product. The crude product was purified by distillation under a reduced pressure of 0.5 Torr at 199° C. and, thus, 136 g (0.25 mol, yield of 87%) of a transparent liquid was obtained. This product was subjected to gas chromatography and the purity of the product was 99.6%.

Example 9

2,7-dibromo-9,9-didodecylfluorene

In a two-liter flask having four openings equipped with a stirrer, a thermometer, a dropping funnel, and a reflux condenser, respectively, 261 g (0.52 mol) of 9,9-didodecylfluorene, 1 L of water, and five drops of sulfuric acid were placed and stirred to mix. By adding 200 g (1.3 mol) of bromine into the mixture, a reaction was started. After the reaction had been conducted at 60° C. for 12 hours, unreacted bromine was decomposed with an aqueous solution of sodium hydrogen sulfite. The target product was extracted from the reaction mixture using hexane, and then washed with water and a sodium hydrogencarbonate aqueous solution. The resulting organic liquid was dried using anhydrous magnesium sulfate. After filtration, the liquid was concentrated and then allowed to stand at 0° C., so that a white solid was precipitated. The precipitate was filtered and subsequently washed with hexane, followed by drying. Thus, 312 g (0.47 mol, yield of 93%) of a white solid product was obtained. This product was subjected to gas chromatography and the purity of the product was 99.0%.

Example 10

2-bromo-9,9'-spirobifluorene

In a two-liter flask having four openings equipped with a stirrer, a thermometer, a dropping funnel, and a reflux condenser, respectively, 1 L of water, three drops of a surfactant, 10.7 g (0.0395 mol) of anhydrous iron (III) chloride, and 253 g (0.8 mol) of 9,9'-spirobifluorene were placed and stirred to mix. By adding 102 g (0.638 mol) of bromine into the mixture, a reaction was started. After the reaction had been conducted at room temperature for 3 hours, unreacted bromine was decomposed with an aqueous solution of sodium hydrogen sulfite. The reaction product, which was a solid, was filtered and washed with water. Thus, 298 g of a crude product was obtained. The crude product was recrystallized using dioxane, thus resulting in 245 g (0.62 mol, yield of 78%) of a white solid, which is the target product. This product was subjected to gas chromatography and the purity of the product was 99%.

Example 11

2,2',7-tribromo-9,9'-spirobifluorene

In a two-liter flask having four openings equipped with a stirrer, a thermometer, a dropping funnel, and a reflux condenser, respectively, 1 L of water, three drops of a surfactant, 10.7 g (0.0395 mol) of anhydrous iron (III) chloride, and 253 g (0.8 mol) of 9,9'-spirobifluorene were placed and stirred to mix. By adding 447 g (2.8 mol) of bromine into the mixture, a reaction was started. After the reaction had been conducted at room temperature for 3 hours, unreacted bromine was decomposed with an aqueous solution of sodium hydrogen sulfite. The reaction product, which was a solid, was filtered and washed with water. Thus, 412 g of a crude product was obtained. The crude product was recrystallized using dioxane, thus resulting in 332 g (0.6 mol, yield of 75%) of a white solid, which is the target product. This product was subjected to gas chromatography and the purity of the product was 99%.

Example 12

2,2',7,7'-tetrabromo-9,9'-spirobifluorene

In a two-liter flask having four openings equipped with a stirrer, a thermometer, a dropping funnel, and a reflux condenser, respectively, 1 L of water, three drops of a surfactant, 10.7 g (0.0395 mol) of anhydrous iron (III) chloride, and 253 g (0.8 mol) of 9,9'-spirobifluorene were placed and stirred to mix. By adding 767 g (4.8 mol) of bromine into the mixture, a reaction was started. After the reaction had been conducted at room temperature for 3 hours, unreacted bromine was decomposed with an aqueous solution of sodium hydrogen sulfite. The reaction product, which was a solid, was filtered and washed with water. Thus, 481 g of a crude product was obtained. The crude product was recrystallized using dioxane, thus resulting in 394 g (0.62 mol, yield of 78%) of a white solid, which is the target product, was obtained. This product was subjected to gas chromatography and the purity of the product was 99%.

As described above, in the method of the present invention, no environmentally harmful organic solvent requiring a high cost to dispose of is used in the bromination. Therefore bromofluorenes can be efficiently and economically prepared.

What is claimed is:

1. A method for preparing bromofluorenes comprising the steps of:

dispersing a compound selected from the group consisting of fluorene, fluorenone, and derivatives of fluorene and fluorenone in water to prepare a disperse system; and adding bromine $Br_2$ into the disperse system to conduct bromination.

2. A method according to claim 1, wherein the bromination is conducted in a reaction system not containing any organic solvent.

3. A method according to claim 1, wherein the resulting bromofluorene is 2,7-dibromofluorene.

4. A method according to claim 1, wherein the resulting bromofluorene is 2,7-dibromo-9,9-dialkylfluorene.

5. A method according to claim 1, wherein the resulting bromofluorene is bromospirobifluorene.

* * * * *